United States Patent
Li et al.

(10) Patent No.: US 11,697,685 B2
(45) Date of Patent: Jul. 11, 2023

(54) CHIMERIC ANTIGEN RECEPTOR CELLS TARGETING ROBO1, PREPARATION METHOD AND USE THEREOF

(71) Applicant: Asclepius (Suzhou) Technology Company Group Co., Ltd., Suzhou (CN)

(72) Inventors: Huashun Li, Suzhou (CN); Baolei Wang, Suzhou (CN); Kunkun Han, Suzhou (CN)

(73) Assignee: Asclepius (Suzhou) Technology Company Group Co., Ltd., Suzhou (CN)

( * ) Notice: Subject to any disclaimer, the term of this patent is extended or adjusted under 35 U.S.C. 154(b) by 644 days.

(21) Appl. No.: 16/700,401

(22) Filed: Dec. 2, 2019

(65) Prior Publication Data

US 2020/0087397 A1 Mar. 19, 2020

Related U.S. Application Data

(63) Continuation of application No. PCT/CN2017/089517, filed on Jun. 22, 2017.

(30) Foreign Application Priority Data

Jun. 2, 2017 (CN) .......................... 201710407619.8

(51) Int. Cl.
| | |
|---|---|
| C07K 16/28 | (2006.01) |
| C07K 14/705 | (2006.01) |
| C12N 5/0783 | (2010.01) |
| A61K 35/17 | (2015.01) |
| A61P 35/00 | (2006.01) |
| C07K 14/725 | (2006.01) |
| C12N 15/867 | (2006.01) |
| A61K 38/00 | (2006.01) |
| A61K 39/00 | (2006.01) |

(52) U.S. Cl.
CPC .......... *C07K 16/2803* (2013.01); *A61K 35/17* (2013.01); *A61P 35/00* (2018.01); *C07K 14/7051* (2013.01); *C07K 14/70517* (2013.01); *C07K 14/70521* (2013.01); *C07K 14/70578* (2013.01); *C12N 5/0646* (2013.01); *C12N 15/867* (2013.01); *A61K 38/00* (2013.01); *A61K 2039/505* (2013.01); *C07K 2317/24* (2013.01); *C07K 2317/55* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 5/0636* (2013.01); *C12N 2510/00* (2013.01)

(58) Field of Classification Search
None
See application file for complete search history.

(56) References Cited

FOREIGN PATENT DOCUMENTS

| CN | 104114233 A | 10/2014 |
|---|---|---|
| CN | 105132445 A | 12/2015 |
| CN | 105392888 A | 3/2016 |
| CN | 105505869 A | 4/2016 |
| CN | 105907719 A | 8/2016 |
| CN | 106317228 A | 1/2017 |
| CN | 106399255 A | 2/2017 |
| WO | 2015142675 A2 | 9/2015 |

OTHER PUBLICATIONS

Patent Cooperation Treaty, International Search Report, Int'l App. No. PCT/CN2017/089517, Applicant: Asclepius (Suzhou) Technology Company Group Co. Ltd., dated Feb. 7, 2018.
Patent Cooperation Treaty, International Preliminary Report on Patentability & Written Opinion of the ISR, Int'l App. No PCT/CN2017/089517, Applicant: Asclepius (Suzhou) Technology Company Group Co. Ltd., dated Feb. 7, 2018.
Liza B. John et al., "Blockade of PD-1 Immunosuppression Boosts CAR T-Cell Therapy," Journal of Oncoimmunology, vol. 2, No. 10, Article e26286, Oct. 10, 2013.
Nan Chen et al., "CAR T-Cell Intrinsic PD-1 Checkpoint Blockade: A Two-In-One Approach for Solid Tumor Immunotherapy," Journal of Oncoimmunology, vol. 6, No. 2, Article e1273302, Dec. 23, 2016.
Roy L. Maute et al., "Engineering High-Affinity PD-1 Variants for Optimized Immunotherapy and Immuno-PET Imaging," PNAS Early Edition 112, E6506-E6514, Nov. 24, 2015.
Hui Qiu et al., "Regulatory Effect of Secretory Recombinant Peptide PD-1-Cell on the Function of Immune Cells and its Anti-Tumor Effect," China Journal of Microbial Immunology, vol. 26, No. 12, Dec. 26, 2006.

*Primary Examiner* — Sharon X Wen
(74) *Attorney, Agent, or Firm* — Flener IP & Business Law; Zareefa B. Flener

(57) ABSTRACT

The present invention relates to chimeric antigen receptor cells targeting ROBO1, in particular, enhanced CAR-T cells and CAR-NK cells targeting ROBO1, and preparation and application thereof. The cells can stably expressing CAR elements, while secreting extracellular domain molecules expressing PD-1 protein or mutants thereof, and thus may block PD-11PD-L1 molecular interaction. It has been found through animal experiments that the cells have very good anti-tumor effects, and the above-mentioned cells can significantly reduce tumor recurrence and improve the survival rate compared with the conventional ROBO1-targeted CAR modified cells.

8 Claims, 4 Drawing Sheets
Specification includes a Sequence Listing.

CHIMERIC ANTIGEN RECEPTOR CELLS TARGETING ROBO1, PREPARATION METHOD AND USE THEREOF

CROSS-REFERENCE TO RELATED APPLICATION

This application is a continuation application of International patent application No. PCT/CN2017/089517, filed on Jun. 22, 2017, which claims the benefit and priority of Chinese patent application No. CN201710407619.8, filed on Jun. 2, 2017, which is incorporated herein by reference in its entirety and for all purposes.

FIELD OF THE INVENTION

The invention relates to the technical field of biotechnology, and in particular relates to a chimeric antigen receptor cell targeting ROBO1, especially, a ROBO1-targeted reinforced CAR-T cell and CAR-NK cell, and preparation method and use thereof.

BACKGROUND OF THE INVENTION

Chimeric antigen receptor modified T cells (CAR-T) immunotherapy is an adoptive immunotherapy rapidly developed in recent years, wherein the CAR is usually comprises of an antigen-binding domain, a transmembrane domain, a costimulatory signaling region and the like, and gene modification technology is adopted, the antibody capable of recognizing the tumor-related antigens is fused and expressed on the surface of the autologous T cells, therefore, the modified T cells have targeted killing effects on tumor cells. The CAR-T therapy has remarkable therapeutic effect on acute leukemia and non-Hodgkin's lymphoma, and is considered to be one of the most promising tumor treatments. In addition to blood system tumors, researchers continue working to extend CAR-T treatment to solid tumors, but no expected therapeutic effect has been obtained when the CAR-T is used for treating solid tumors (which are composed of heterogeneous cell populations, the heterogeneous cells having different surface molecules), and an ideal treatment effect is not obtained.

PD-L1 is short for programmed death receptor-Ligand 1, also referred as programmed cell death-Ligand1, and is the first type transmembrane protein with 40 k Da in size. PD-1 is short for programmed death receptor 1, also referred as programmed death 1, and is an important immunosuppression molecule, it is a member of CD28 superfamily. PD-1 is mainly expressed on the surface of T cells and primary B cells, the two ligands of PD-1 (PD-L1 and PD-L2) are widely expressed in antigen presenting cell (APC) and the like. The interaction between PD-1 and the ligands thereof plays an important role in the aspect of negative regulation of immune responses. The expression of PD-L1 protein can be detected in many human tumor tissues, and the microenvironment at the tumor site can induce expression of PD-L1 on tumor cells. The expressed PD-L1 facilitates the occurrence and growth of tumors, induces the apoptosis of the anti-tumor T cells to escape the attack of immune system. The inhibition of the binding of PD-1 to the ligands can expose the tumor cells to the killing power of immune system, so that the effects of killing tumor tissues and treating cancers can be achieved.

At the 2016 AACR® (American Association for Cancer Research) annual conference, it is reported by the Professor of dermatology Paul T. Nghiem, MD, PhD, School of Medicine, University of Washington that pembrolizumab, a monoclonal antibody with the anti-PD-1 effect, can induce high-reactivity of advanced Merkel cell carcinoma, its median progression-free survival (PFS) is 9 months, while the PFS of traditional chemotherapy is three months. Recently, a new progress has been made for a PD-1 inhibitor OPDIVO® by Bristol-Myers™ in the aspect of clinical tests, and two sets of data are issued, wherein one set of data shows that patients with advanced melanoma who have no treatment response to any current drug have achieved a 34% five-year survival rate with OPDIVO®. It should be noted that the five-year survival rate of the IV-stage melanoma patients is usually only 15% to 20%. The other set of data show that the combination use of OPDIVO® and YERVOY® can achieve 22% overall response rate, and 69% overall two-year survival rate in patients with advanced melanoma. It show in another study that the survival time and survival rate of patients who suffered from refractory relapsed or metastatic head and neck squamous cell carcinoma (SCCHN) are greatly improved after treatment by OPDIVO®. The data show that compared with a control group, the death risk of the OPDIVO® treatment group is remarkably reduced by 30%, and the median overall survival time is remarkably prolonged. The one-year survival rate of the OPDIVO® treatment group is 36%, while the control group is 16.6%. In addition, the therapeutic effect of the OPDIVO® vs the control scheme is evaluated in terms of the status of the mouth-throat tumor HPV and the expression status of the PD-L1 in the study. Recently, KEYTRUDA® has been approved by FDA® (Food and Drug Administration) as a breakthrough drug for the treatment of relapsed or refractory (R/R) typical Hodgkin's lymphoma (cHL).

The patent application CN1055058669A discloses chimeric receptor T cells for tumor stem cells. The T cells are embedded with 2-3 independent antigen receptors, and each chimeric antigen receptor is formed by antigen-binding sites of antibody against specific marker to different tumor stem cells and different functional proteins, respectively. The chimeric receptor T cells can only activate anti-tumor effects of T cell after the antigen is recognized by the said 2-3 chimeric antigen receptors. The method has improved the specificity to a certain extent, but is less specific for tumor cells with hidden antigens.

It is reported in a literature by Liza B. John (Blockade of PD-1 immunosuppression boosts CAR-T-cell therapy) that the PD-1 immunosuppression pathway, namely the binding of PD-1 to ligand PD-L, is hindered by the addition of an anti-PD-1 antibody, thereby, the anti-tumor effect of the genetically modified chimeric antigen-expressing receptor T cells (CAR-T) is improved to a certain extent.

SUMMARY OF THE INVENTION

In order to overcome the defects in the prior art, the invention provides a chimeric antigen receptor cell targeting ROBO1, and particularly a ROBO1-targeted reinforced CAR-T cell and a CAR-NK cell, and preparation method and use thereof.

A study finds that Robo1 is over-expressed in a variety of cancers, such as hepatocellular carcinoma, breast cancer, colon cancer, pancreatic cancer, prostate cancer, neuroglioma and the like, while it is expressed at low level in normal tissues. Thus it can be used as a new tumor-related antigen and is a potential treatment and diagnosis target.

In the first aspect of the present invention, it provides a encoding nucleotide comprising a nucleotide encoding chimeric antigen receptor and a nucleotide encoding extracellular secretory protein, wherein the chimeric antigen receptor comprises an antigen-binding domain, a transmembrane domain and a costimulatory signaling region, and the antigen-binding domain is capable of specifically binding tumor specific antigen ROBO1, and activating immune cells (such as T cells, B cells or natural killer cells) through the transmembrane domain and the costimulatory signaling region; the extracellular secretory protein is capable of preventing or inhibiting the binding of the wild type PD-1 protein to the PD-L1 ligand.

Preferably, the nucleotide encoding chimeric antigen receptor and the nucleotide encoding extracellular secretory protein are not in the same reading frame.

In one embodiment of the present invention, the extracellular secretory protein is PD-1 fragment binding to PD-L1 and/or PD-L2.

In a preferred embodiment of the present invention, the extracellular secretory protein is an extracellular domain or a mutant sequence of the PD-1 protein, wherein the mutant of the extracellular domain is capable of binding PD-L1 with high affinity. preferably, the extracellular domain or the mutant of the PD-1 protein has an amino acid sequence as shown in SEQ ID NO: 8.

In a preferred embodiment of the invention, the nucleotide encoding extracellular domain or the mutant of the PD-1 protein has a sequence as shown in SEQ ID NO: 1. The extracellular region of the Robo1 comprises five immunoglobulin conserved regions (designated as IG 1-5 respectively)) and three FibronectinIII type repetitive sequences (designated as FNIIII 1-3, or FN1-3 for short), and the intracellular region comprises four conserved regions (designated as CC0, CC1, CC2 and CC3 respectively). The antigen-binding domain can specifically bind to one or more of the IG1, IG2, IG3, IG4, IG5, FN1, FN2 and FN3 domains of the tumor specific antigen ROBO1.

In one embodiment of the present invention, in the encoding nucleotide, the antigen-binding domain is capable of specifically binding to the FN3 domain of the tumor specific antigen ROBO1 (hereinafter referred to as ROBO1-FN3 for short).

In one embodiment of the invention, in the encoding nucleotide, the antigen-binding domain is an antibody or an antigen-binding fragment thereof; preferably, the antigen-binding domain is an antibody or antigen-binding fragment thereof specifically binding to FN3 domain of ROBO1.

In one embodiment of the invention, in the encoding nucleotide, the antigen-binding fragment is Fab or scFv.

In one embodiment of the invention, in the encoding nucleotide, the antigen-binding domain is an anti-ROBO1-FN3scFv. Preferably, the anti-ROBO1-FN3 scFv has an amino acid sequence as shown in SEQ ID NO: 9.

In a preferred embodiment of the invention, in the encoding nucleotide, the antigen-binding domain is an anti-ROBO1-FN3scFv, the nucleotide encoding antigen-binding domain has a sequence as shown in SEQ ID NO: 2.

In one embodiment of the invention, the encoding nucleotide further comprises internal ribosome entry site IRES nucleotide, and the IRES nucleotide is located between the nucleotide encoding chimeric antigen receptor and the nucleotide of the encoding extracellular secretory protein; preferably, the IRES nucleotide has a sequence as shown in SEQ ID NO: 3.

In one embodiment of the present invention, the encoding nucleotide comprises a nucleotide encoding extracellular domain of the IRES-PD-1 protein or the mutant thereof.

In one embodiment of the present invention, in the encoding nucleotide, the transmembrane domain is selected from one or more transmembrane domains of CD28, CD3E, CD45, CD4, CD5, CD8, CD9, CD16, CD22, CD33, CD37, CD134, CD137, ICOS and CD154.

In one preferred embodiment of the invention, in the encoding nucleotide, the transmembrane domain is a CD8 transmembrane ($CD8^{TM}$) domain.

In one embodiment of the invention, the $CD8^{TM}$ domain has a sequence as shown in SEQ ID NO: 10.

In a preferred embodiment of the invention, the nucleotide encoding $CD8^{TM}$ domain has a sequence as shown in SEQ ID NO: 4.

In one embodiment of the present invention, the costimulatory signaling region comprises intracellular domains of costimulatory molecules, preferably, the costimulatory molecule is selected from one or more of CD3ζ, CD3γ, CD3δ, CD3ε, CD5, CD22, CD79a, CD79b, CD66d, CD2, CD4, CD5, CD28, CD134, CD137, ICOS, CD154, 4-1BB and OX40.

In one preferred embodiment of the invention, in the encoding nucleotide, the costimulatory signaling region comprises 4-1BB and CD3ζ intracellular domains.

In one embodiment of the invention, the 4-1BB intracellular domain has a sequence as shown in SEQ ID NO: 11.

In another embodiment of the present invention, the CD3ζ intracellular domain has a sequence as shown in SEQ ID NO: 12.

In one embodiment of the invention, the nucleotide encoding 4-1BB intracellular domain has a sequence as shown in SEQ ID NO: 5.

In another embodiment of the invention, the nucleotide encoding CD3ζ intracellular domain has a sequence as shown in SEQ ID NO: 6.

In a preferred embodiment of the invention, the encoding nucleotide comprises the nucleotide encoding CD8 transmembrane domain, 4-1BB and CD3ζ intracellular domains.

In a more preferred embodiment of the invention, the encoding nucleotide comprises a nucleotide encoding $CD8^{TM}$-4-1BB-CD3ζ.

In a further preferred embodiment of the invention, the encoding nucleotide comprises a nucleotide encoding anti-ROBO1-FN3 scFv-$CD8^{TM}$-4-1BB-CD3ζ, preferably, the nucleotide encoding anti-ROBO1-FN3 scFv-$CD8^{TM}$-4-1BB-CD3ζ has a sequence as shown in SEQ ID NO: 13.

In one embodiment of the invention, the encoding nucleotide sequence is isolated and/or synthesized.

In a preferred embodiment of the invention, the encoding nucleotide comprises a nucleotide encoding anti-ROBO1-FN3 scFv-$CD8^{TM}$-4-1BB-CD3ζ-IRES-(PD-1 protein extracellular domain or mutant thereof), preferably, the nucleotide encoding anti-ROBO1-FN3 scFv-$CD8^{TM}$-4-1BB-CD3ζ-IRES-(PD-1 protein extracellular domain or mutant thereof), has a sequence as shown in SEQ ID NO: 7.

In the second aspect of the invention, it provides a vector containing the encoding nucleotide described in the invention.

In one embodiment of the invention, the vector is selected from one or more of plasmids, bacteria, viruses and the like.

In one embodiment of the present invention, as for the vector, a virus vector which lacks replication capability and cannot be self-replicated in transfected cells can be used, such as reverse transcription virus vectors (including oncogenic retroviral vectors, lentivirus vectors and pseudo type vectors), adenovirus vectors, vaccinia virus vectors or HSV vectors and the like.

In one preferred embodiment of the invention, the vector is a lentivirus vector.

In a more preferred embodiment of the present invention, the lentiviral vector is a PRRSLIN vector.

In one embodiment of the invention, the vector further comprises a promoter.

In a preferred embodiment of the invention, the promoter is EF-1α promoter.

In the third aspect of the invention, it provides chimeric antigen receptor cells (CAR-cells), which expresses an extracellular secretory protein, wherein the extracellular secretory protein can prevent or inhibit the binding of the wild type PD-1 protein to the PD-L1 ligand.

In one embodiment of the present invention, in the CAR-cell, the extracellular secretory protein is PD-1 protein fragment binding to PD-L1 and/or PD-L2.

In a preferred embodiment of the present invention, in the CAR-cell, the extracellular secretory protein is an extracellular domain of the PD-1 protein or a mutant sequence thereof, preferably, the extracellular domain of the PD-1 protein or the mutant thereof has an amino acid sequence as shown in SEQ ID NO: 8.

In a preferred embodiment of the invention, in the CAR-cells, the nucleotide encoding extracellular domain of the PD-1 protein or the mutant thereof has a sequence as shown in SEQ ID NO: 1.

Preferably, the CAR-cell further expresses a chimeric antigen receptor, wherein the chimeric antigen receptor comprises an antigen-binding domain, a transmembrane domain, and a costimulatory signaling region, the antigen-binding domain can specifically bind the tumor specific antigen ROBO1, and activate the CAR-cells (e.g. CAR-T cells, B cells or natural killer cells) through the transmembrane domain and the costimulatory signaling region.

In one embodiment of the present invention, in the CAR-cells, the antigen-binding domain can specifically bind to one or more of the Ig1, Ig2, Ig3, Ig4, Ig5, FN1, FN2 and FN3 domains of the tumor specific antigen ROBO1.

In one embodiment of the invention, in the CAR-cells, the antigen-binding domain in the CAR-cell can specifically bind to the tumor specific antigen ROBO1-FN3.

In one embodiment of the invention, in the CAR-cells, the antigen-binding domain is an antibody or antigen-binding fragment thereof. Preferably, the antigen-binding domain is an antibody or antigen-binding fragment thereof specifically binding to FN3 domain of ROBO1.

In one embodiment of the invention, in the CAR-cell, the antigen-binding fragment is Fab or scFv.

In one embodiment of the invention, in the CAR-cell, the antigen-binding domain is anti-ROBO1-FN3scFv; preferably, the anti-ROBO1-FN3scFv has an amino acid sequence as shown in SEQ ID NO: 9; more preferably, the nucleotide encoding antigen-binding domain has a sequence as shown in SEQ ID NO: 2.

In one embodiment of the present invention, in the CAR-cells, internal ribosome entry site IRES nucleotide is located between the nucleotide encoding chimeric antigen receptor and the nucleotide encoding extracellular secretory protein, and has a sequence as shown in SEQ ID NO: 3.

In one embodiment of the present invention, in the CAR-cells, the transmembrane domain is selected from one or more transmembrane domains of CD28, CD3ε, CD45, CD4, CD5, CD8, CD9, CD16, CD22, CD33, CD37, CD134, CD137, ICOS and CD154.

In one preferred embodiment of the invention, in the encoding nucleotide, the transmembrane domain is CD8 transmembrane (CD8$^{TM}$) domain.

In one embodiment of the invention, the CD8$^{TM}$ domain has a sequence as shown in SEQ ID NO: 10.

In a preferred embodiment of the invention, the nucleotide encoding the CD8$^{TM}$ domain has a sequence as shown in SEQ ID NO: 4.

In one embodiment of the present invention, the costimulatory signaling region comprises intracellular domains of costimulatory molecules, preferably, the costimulatory molecule is selected from one or more of CD3ζ, CD3γ, CD35, CD3ε, CD5, CD22, CD79a, CD79b, CD66d, CD2, CD4, CD5, CD28, CD134, CD137, ICOS, CD154, 4-1 BB and OX40.

In one preferred embodiment of the invention, in the encoding nucleotide, the costimulatory signaling region comprises 4-1BB and CD3ζ intracellular domains.

In one embodiment of the invention, the 4-1BB intracellular domain has a sequence as shown in SEQ ID NO: 11.

In another embodiment of the present invention, the CD3ζ intracellular domain has a sequence as shown in SEQ ID NO: 12.

In one embodiment of the invention, the nucleotide encoding 4-1BB intracellular domain has a sequence as shown in SEQ ID NO: 5.

In another embodiment of the invention, the nucleotide encoding CD3ζ intracellular domain has a sequence as shown in SEQ ID NO: 6.

In a preferred embodiment of the invention, the encoding nucleotide comprises the nucleotide encoding CD8 transmembrane domain, 4-1 BB and CD3ζ intracellular domains.

In a more preferred embodiment of the present invention, the CAR-cells comprise the nucleotide encoding CD8$^{TM}$-4-1BB-CD3ζ.

In a further preferred embodiment of the invention, the CAR-cells comprise a nucleotide encoding anti-ROBO1-FN3 scFv-CD8$^{TM}$-4-1BB-CD3ζ, preferably, the anti-ROBO1-FN3 scFv-CD8$^{TM}$-4-1BB-CD3ζ has a sequence as shown in SEQ ID NO: 13.

In a preferred embodiment of the present invention, the CAR-cells comprise a nucleotide encoding anti-ROBO1-FN3 scFv-CD8$^{TM}$-4-1BB-CD3ζ-IRES-(PD-1 protein extracellular domain or mutant thereof), and preferably, the anti-ROBO1-FN3 scFv-CD8$^{TM}$-4-1BB-CD3ζ-IRES-(PD-1 protein extracellular domain or mutant thereof), has a sequence as shown in SEQ ID NO: 7.

In one embodiment of the present invention, the CAR-cells comprise the encoding nucleotide described in the first aspect of the present invention.

In one embodiment of the present invention, the CAR-cells comprise the vector described in the second aspect of the invention.

In one embodiment of the invention, the CAR-cells are immune cells, and are selected from one or more of T cells, natural killer (NK) cells, cytotoxic T lymphoma cells and regulatory T cells.

In one embodiment of the present invention, the T cells are human T cells, preferably, the human is a person with cancer.

In one embodiment of the present invention, the NK cells are human NK cells, preferably, the human is a person with cancer; more preferably, the NK cells are NK92 cells.

In a preferred embodiment of the present invention, the CAR-cells are human T cells (hereinafter referred to as CAR-T cells for short).

In a preferred embodiment of the present invention, the CAR-cells are NK cells (hereinafter referred to as CAR-NK cells for short).

In a more preferred embodiment of the present invention, the CAR-NK cells are CAR-NK92 cells.

The CAR-cells described in the invention can be administrated alone or be administrated as a pharmaceutical composition in combination with other components such as IL-2 or other cytokines or cell populations.

In the fourth aspect of the invention, it provides a method for preparing the above CAR-cells, the method comprises the following steps:

(1) cloning the encoding nucleotide sequence into vectors;
(2) transfecting the vectors obtained in the step (1) into 293T cells to prepare virus;
(3) infecting immune cells by using the virus obtained in the step (2), and making the immune cells express the chimeric antigen receptor and the extracellular domain of the extracellular secreted PD-1 protein or the mutant protein thereof to obtain CAR-cells.

In the fifth aspect of the invention, it provides a pharmaceutical composition comprising one or more of the encoding nucleotide, the vector and the CAR-cell of the invention.

In one embodiment of the present invention, the pharmaceutical composition comprises an effective amount of CAR-cells, preferably CAR-T cells and/or CAR-NK92 cells.

In one embodiment of the invention, the pharmaceutical composition further comprises pharmaceutically acceptable excipients.

In one embodiment of the invention, in the pharmaceutical composition, the excipients are selected from one or more of buffer solution, carbohydrates, antioxidants, chelating agents and preservatives. The pharmaceutical composition described in the present invention is preferably formulated for intravenous administration.

The pharmaceutical composition can be administrated in any convenient manner, including spraying, injection, oral administration, infusion, implantation or transplantation, and preferably, the pharmaceutical composition described in the present invention can be administrated to the patients subcutaneously, intradermally, intra-tumor, intra-knot, intra-spinal, intramuscularly, intravenously or intraperitoneally. In one embodiment of the present invention, the pharmaceutical composition is administered to a patient by intravenous injection (i.v.).

In the sixth aspect of the invention, it provides a use of one or more of the encoding nucleotides, vectors, CAR-cells and pharmaceutical compositions in preparation of a medicament for treating and/or preventing cancer.

In one embodiment of the invention, in the use, the cancer is tumor with high expression of ROBO1 and related diseases, the "high expression" means that the expression level of the ROBO1 in the tumor cells is higher than that in normal cells.

In one embodiment of the invention, the cancer is liver cancer, breast cancer, colon cancer, pancreatic cancer, prostate cancer, neuroglioma or lung cancer.

In a preferred embodiment of the invention, the cancer is a lung cancer.

On the basis of previous research work (as in the Chinese patent application No. CN201610237593.2), the inventors prepare a chimeric antigen receptor cell targeting ROBO1, and provide the preparation and use thereof, in particularly, enhanced CAR-T cell and a CAR-NK targeting ROBO1. The cells above can stably express CAR elements, while secret extracellular domain molecules expressing PD-1 protein or mutants thereof, which may block the interaction of PD-1/PD-L1 molecules. It has been found through animal experiments that the cells have excellent anti-tumor effects.

The above cells can significantly reduce tumor recurrence rate and improve the survival rate compared with the conventional ROBO1-targeted CAR modified cells.

BRIEF DESCRIPTION OF THE DRAWINGS

FIG. 2-B illustrates virus-infected T cells.

FIG. 3-B illustrates NK-92 cells that are infected by the virus and then subjected to a flow sort and cultured for 1 month.

DETAILED DESCRIPTION OF THE INVENTION

Figure 1:
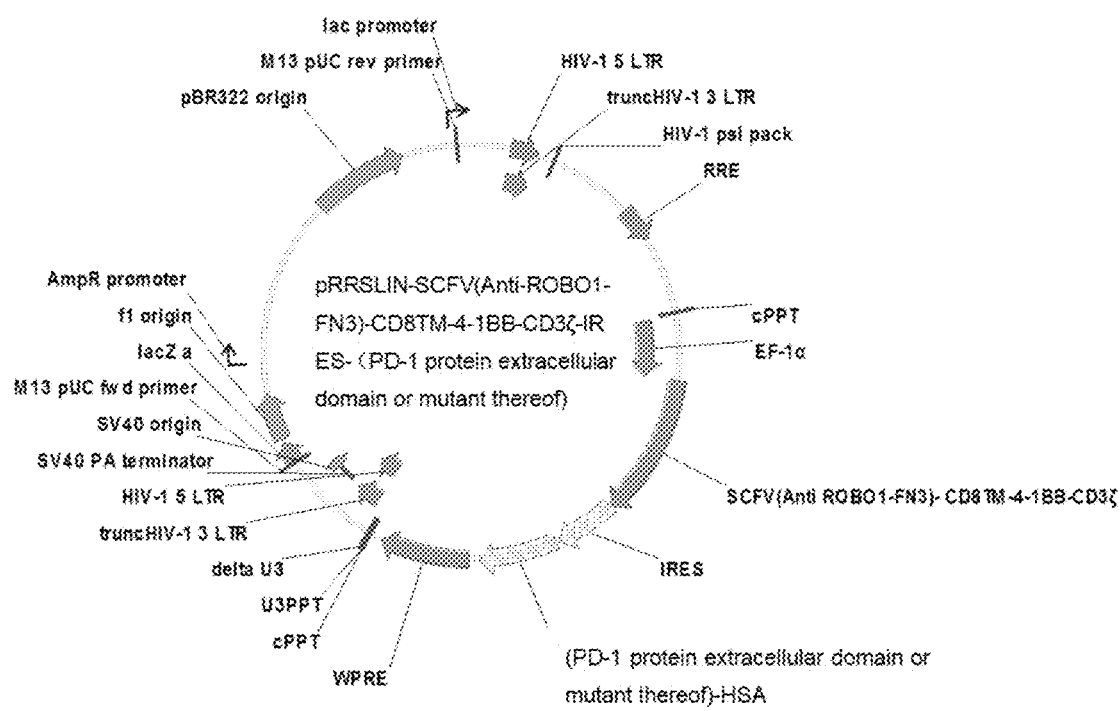
FIG. 1 illustrates a schematic construction map of a lentiviral expression vector provided in Example 1 of the present invention.

Unless otherwise defined, all technical and scientific terms used in the present invention have the same meaning as commonly understood by one of ordinary skill in the technical field of the invention.

In the present invention, the term "antibody" refers to an immunoglobulin molecule specifically binding to an antigen. An antibody may be an intact immunoglobulin derived from natural source or recombinant source, and may be the immune response portion of intact immunoglobulin. The antibody is usually a tetramer of immunoglobulin molecules. The antibodies of the invention may be present in a variety of forms, including polyclonal antibodies, monoclonal antibodies, FV, Fab and F(ab)$_2$, and a single-chain antibody and a humanized antibody, etc (Harlow et al. 1999, in: Using Antibodies: A Laboratory Manual, Cold Spring Harbor Laboratory Press, NY; Harlow et al. 1989, In: Antibodies: A Laboratory Manual, Cold Spring Harbor, New York; Houston et al. 1989, Proc. Natl. Acad. Sci. USA 85; 5879-5883; Bird et al. 1988, Science 242: 423-426).

The term "antibody fragment" refers to a part of an intact antibody, and refers to an antigen-determinant variable region of an intact antibody. Examples of antibody fragments include, but are not limited to, Fab, Fab', F(ab')2 and Fv fragments, a linear antibody formed from an antibody fragment, a scFv antibody and a multi-specific antibody.

The term "antigen-binding fragment" is composed of an intact light chain, a heavy chain VH and a CHI domain, and can be specifically bind to an antigen.

The term "encoding" refers to the intrinsic properties of specific sequences of nucleotides in polynucleotides such as a gene, cDNA or mRNA used as templates for synthesis of other polymers and macromolecules, wherein the polymers and the macromolecules have any one of a defined sequence of nucleotides (i.e., rRNA, tRNA and mRNA) or an amino acid sequence and biological properties produced by them. Thus, if the transcription and translation of mRNA corresponding to a gene produce a protein in cells or other biological systems, the gene encodes the protein. The nucleotide sequence is equivalent to the mRNA sequence and is generally provided in a coding strand, and a non-coding strand used as a template of a transcription gene or a cDNA in a sequence listing, both of which can be referred to as encoding protein or other product for gene or cDNA.

Unless stated otherwise, "nucleotide sequence encoding amino acid sequence" includes all nucleotide sequences that are degenerate each other and encode the same amino acid sequence. Nucleotide sequences encoding protein and RNA can include introns.

The term "costimulatory molecule" refers to an associated binding chaperone on T cells specifically binding to costimulatory ligand, thereby mediating costimulatory response of T cell, such as, but not limited to, proliferation. Costimulatory molecules include, but are not limited to, MHCI molecules, BTLA and Toll ligand receptors.

The term "lentivirus" refers to a genus of retrovirus, which can effectively infect non-periodic and post-mitotic cells; and it can deliver significant amount of genetic information to the DNA of host cell, so that it is one of the most effective methods of gene delivery vectors.

The term "promoter" is defined as DNA sequence that is necessary for start of specific transcription of polynucleotide sequence, and can be recognized by synthesis machinery of cell, or can direct the synthesis machinery of cell.

The term "specifically binding" refers to recognizing specific antigen but not substantially recognizing or binding other molecules in samples.

The term "vector" is a composition comprising isolated nucleic acids, which can be used to deliver isolated nucleic acids into cells. Many vectors are known in the art, and including but not limited to, linear polynucleotides, polynucleotides associated with ionic or amphiphilic compounds, plasmids, and viruses. Thus, the term "vector" includes autonomously replicating plasmids or viruses. The term should also be interpreted as including non-plasmid and non-viral compound that facilitates delivering nucleic acids into cells, such as, polylysine compounds, liposomes, and the like. Examples of viral vectors include, but are not limited to, adenovirus vectors, adeno-associated virus vectors, reverse transcription virus vectors and the like.

The term "isolated" refers to changing or removing from natural state. For example, nucleic acids or peptides naturally present in living animals are not "isolated", but the same nucleic acid or peptide which is partially or completely separated from the coexisting substance of its natural state is "isolated". The isolated nucleic acid or protein may be present in substantially purified form, or, for example, may be present in non-natural environment, such as a host cell.

The term "cancer" is defined as disease characterized by the rapid and uncontrolled growth of aberrant cells. Cancer cells can spread locally or through the bloodstream and lymph system to other parts of the body. Examples of various cancers include, but are not limited to, breast cancer, prostate cancer, ovarian cancer, cervical cancer, skin cancer, pancreatic cancer, colorectal cancer, kidney cancer, liver cancer, brain cancer, lymphoma, leukemia, lung cancer and the like.

The term "anti-tumor effect" refers to biological effect, which can be manifested by reduction in tumor volume, decrease in the number of tumor cells, decrease in the number of metastases, increase of the expected life, or the improvement of various physiological symptoms associated with the cancer condition.

The terms "patient", "subject" and "individual" and the like can be used interchangeably herein, and refers to any animal or cell that follows the methods described herein, whether in vitro or in situ. In some non-limiting embodiments, patients, subjects, or individuals are human.

The "-" linkage of the amino acid sequence of the present invention is that the N-terminus of one fragment is directly linked to the C-terminus of the other fragment, and no linker peptide exists in the middle.

The technical solutions of the present invention will be clearly and completely described below with reference to the Examples of the present invention, the Examples described are merely a part of the embodiments of the present invention rather than all of the embodiments. Based on the Examples of the present invention, all other embodiments obtained by ordinary skilled persons in the field without inventive efforts shall fall within the protection scope of the present invention.

Example 1: Preparation of Lentiviral Expression Vector

According to the sequence information of PD-1 mutant molecule(HAC) reported by "Engineering high-affinity PD-1 variants for optimized immunotherapy and immune-PET imaging" (Maute R L, Gordon S R, Mayer A T, et al. Proceedings of the National Academy of Sciences, 2015, 112(47): E6506-E6514.), the gene sequence of PD-1 protein extracellular domain or mutant thereof was synthesized, as shown in SEQ ID NO: 1. Based on Genebank database the following sequences were searched and synthesized: the known human anti-ROBO1-FN3scFv (hereinafter referred to as scFv for short) gene sequence, IRES inner ribosome entry site, human CD8 transmembrane region gene sequence, human 4-1BB intracellular region gene sequence, and CD3ζ intracellular region gene sequences were shown in SEQ ID NO: 2-6, respectively.

The above gene sequences were sequentially linked in the order of scFv gene, CD8 gene, human 4-1BB intracellular region gene and CD3ζ intracellular region, IRES ribosome internal ribosome entry site, and the extracellular domain of PD-1 protein or the mutant gene thereof, and different restriction enzyme sites were introduced at the linking positions of the sequences, so as to form an intact scFv-CD8$^{TM}$-4-1BB-CD3ζ-IRES-(the PD-1 protein extracellular domain or mutant thereof) gene sequence as shown in SEQ ID NO: 7.

The scFv-CD8$^{TM}$-4-1BB-CD3ζ-IRES-(the extracellular domain of the PD-1 protein or mutant thereof) gene sequence was transformed into a pRRSLIN vector by double enzyme digestion, wherein the upstream of the gene was an EF-1α promoter. After the vector was transformed into Stbl3 *Escherichia coli* strain, the strain was transferred to solid culture medium containing ampicillin to culture, and screened to obtain positive clones. Plasmids were extracted, and identified by enzyme digestion, and the vectors were successfully constructed through sequencing to obtain a pRRSLIN-scFv-CD8$^{TM}$-4-BB-CD3ζ-IRES-(PD-1 protein extracellular domain or mutant thereof) lentivirus expression vector. The construction map of the lentivirus expression vector is shown in FIG. 1.

Example 2: Preparation of Lentivirus 1. 24 Hours before transfection, 293T cells were inoculated into a 15 cm culture dish at a cell density of about 8×10$^6$ cells per dish. It was ensured that the cells were at a confluence degree of about 80%, and evenly distributed in the culture dish at the time of the transfection.

2. Preparation of solution A and solution B

Solution A: 6.25 mL 2×HEPES buffer solution (the amount of 5 large vessels for packaging was used for the best effect).

Solution B: A mixture with the following plasmids respectively added: 112.5 μg scFv-CD8$^{TM}$-4-1BB-CD3ζ-IRES-(the PD-1 protein extracellular domain or mutant thereof) (target plasmid), 39.5 μg pMD2.G(VSV-G envelop), 73 μg pCMVR8.74(gag, pol, tat, rev), 625 μL 2M calcium ion solution. The total volume of solution B was 6.25 ml.

3. The solution B was thoroughly mixed, and the solution B was added dropwise to Solution A while the solution A was lightly vortexed, and allowed to stand for 5-15 minutes. The mixed solution of A and B was lightly vortexed, and added dropwise to a culture dish containing 293T cells. The culture dish was slightly shaken back and forth to evenly distribute the mixture of DNA and calcium ions (without rotating the culture dish). The culture dish was placed in an incubator and cultured for 16-18 hours.

The medium was replaced with new fresh culture medium and continued to culture.

It was centrifuged at a rotating speed of 500 g, and temperature of 25° C. for 10 min, and filtered by a PES film (0.45 μm)). A centrifuge tube (Beckmann ultra-clear SW28 centrifuge tube) was sterilized with 70% ethanol, and then disinfected under an ultraviolet lamp for 30 min. The filtered supernatant containing the lentivirus was transferred into the centrifugal tube, and a layer of 20% sucrose (1 mL sucrose/8 mL supernatant was added) was cautiously laid at the bottom of the centrifuge tube, and the centrifuge tube was equilibrated with PBS, and centrifuged at a speed of 25,000 rpm (82, 700 g) for 2 h at 4° C. The centrifuge tube was cautiously taken out, and the supernatant was discarded, and the centrifuge tube was inverted to remove the residual liquid. The centrifugal tube was added 100 μl PBS, sealed, placed at 4° C. for 2 hours with a gentle vortex every 20 minutes, and centrifuged at 500 g for 1 min (25° C.), the lentivirus-containing supernatant was collected, cooled on ice, and then stored at −80° C.

Example 3: Preparation of CAR-T Cells

CAR-T cells were prepared according to the steps of CN20161022230.9 example 3.

Figure 2:
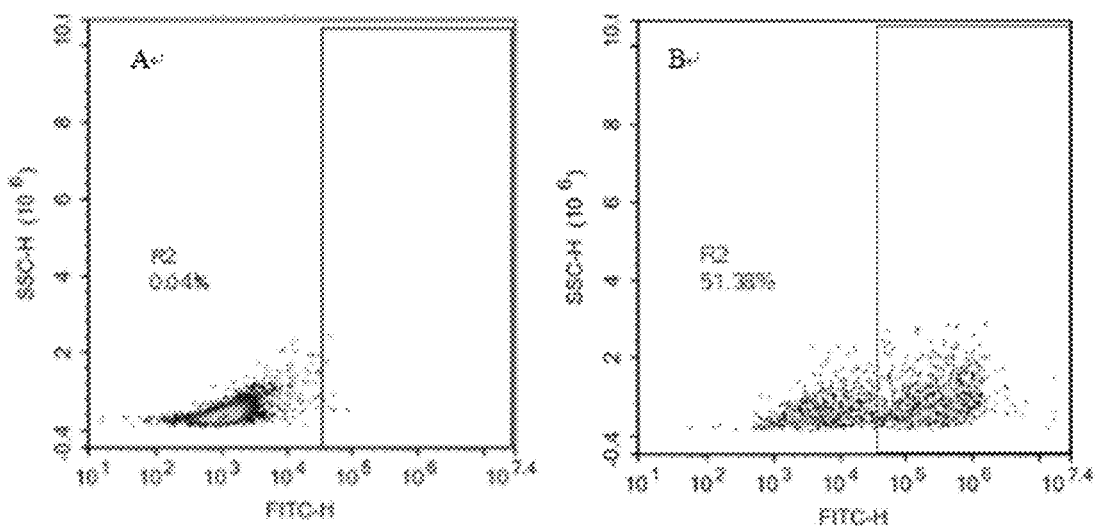
FIG. 2 illustrates a flow cytometry result of CAR-T provided in Example 3 of the present invention, wherein FIG. 2-A illustrates T cells without virus infection, and serve as a control.

CAR-T positive rate was detected by flow cytometry after virus infection, and the flow cytometry detection result is shown in FIG. 2. The result showed that the positive rate was 51.38%, indicating that the CAR-T cells were successfully prepared. (FIG. 2: the detection of CAR-T positive expression rate by flow cytometry, FIG. 2-A illustrates T cells without virus infection, and served as a control, and FIG. 2-B illustrates virus-infected T cells. The antibody was labeled with FITC fluorescent and was represented on the abscissa. If the T cells successfully expressed the CAR molecules, the signal value would significantly increase).

Example 4: Preparation of CAR-NK92 Stable Cell Strain

The density of NK92 cells was adjusted to 2-3×10$^5$/ml. The virus was added to the NK92 cells in the volume ratio (V/V) of virus:cell medium=1:5-10, and the 8 μg/mL polybrene was added at the same time. After 4 hours, the density of the cells was adjusted to 1×10$^5$/mL by supplementally adding equal amount of fresh complete culture medium (The complete culture medium formulation can be found in the instructions of ATCC) for further culture. On the next day, all the cells were centrifuged, fresh culture medium was added to continue to culture. The solution was supplemented every 1-2 days, so that the cell density was maintained at 2-3×10$^5$/ml. After 72 hours, CAR antibody staining was carried out; and CAR-NK-92 positive cells were sorted by flow cytometry for culture expansion. The color change, cell density, and cell morphology of the culture medium were observed and recorded accordingly.

Figure 3:
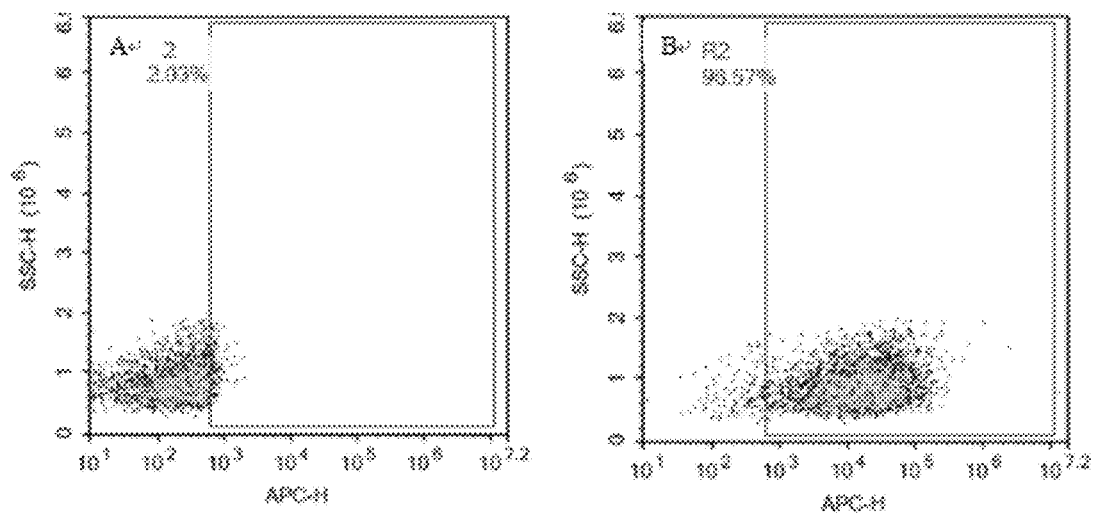
FIG. 3 illustrates a flow cytometry result of CAR-NK-92 provided in Example 4 of the present invention, wherein FIG. 3-A illustrates NK-92 cells without virus infection, and serve as a control.

After flow sorting, positive CAR-NK-92 cells were continuously cultured. After expanding for 1 month, the positive rate of CAR NK-92 cells was detected by flow cytometry, and the flow cytometry detection result is shown in FIG. 3. The result showed that the positive rate of the CAR-NK92 was 96.57%, indicating that NK-92 cells stably expressing CAR element were successfully prepared (FIG. 3: the positive expression rate of CAR-NK-92 was detected by flow cytometry, wherein FIG. 3-A illustrates the NK-92 cells without virus infection, and served as a control; and FIG. 3-B illustrates the NK-92 cells that were infected with virus and then subjected to flow sort and cultured for 1 month. The antibody was labeled with APC fluorescent and was represented on the abscissa. If NK-92 cells successfully expressed the CAR molecules, the signal value would significantly increase).

Example 5. In Vitro Activity Assay of CAR Cells

The killing effect of CAR-T and CAR-NK-92 cells on tumor cells were detected with LDH release method, and LDH release was measured with ELISA.

1. Target cells were adjusted to 5×10$^4$/mL with RPMI-1640 culture solution containing 5% calf serum.

2. The target cells were added into 96-well cell culture plates with 100 μL per well. Three wells were selected as control of spontaneous release of effector cells (CART cells), which were only added 100 μL of culture medium without adding target cells.

3. 100 μL effector cells were added into each well, wherein the ratio of effector cells to target cells was 10:1; 5:1:1. The wells of spontaneous release were added only with 100 μL of culture medium without adding effector cells. The effector cells were co-incubated with target cells for 6 hours; and three replicate wells were used for each experiment.

4. 10 μL Lysis Solution (10×) was added into the largest release well (positive control), and incubated for 45-60 minutes. Meanwhile, three replicate wells were used for each experiment.

5. 50 μL of each of the test sample and the control sample in the above 3 and 4 steps were taken out and added to a fresh 96-well ELISA plate, then reaction solution and substrate were added to stand for 30 minutes in the dark.

6. Adding 50 μL stop solution.

7. The optical density (OD value) of each well was measured on an enzyme-linked detector at 490 nm or 492 nm within 1 hour.

8. Calculation of specific lysis activity killing rate=experimental group LDH(OD)/max LDH release group (OD).

Calculation formula: Specific lysis activity=(experimental group−effect spontaneous release−target spontaneous release)/(target maximum release−target spontaneous release)×100%

9. Determination of cytokine secretion with CBA kit

Figure 4:
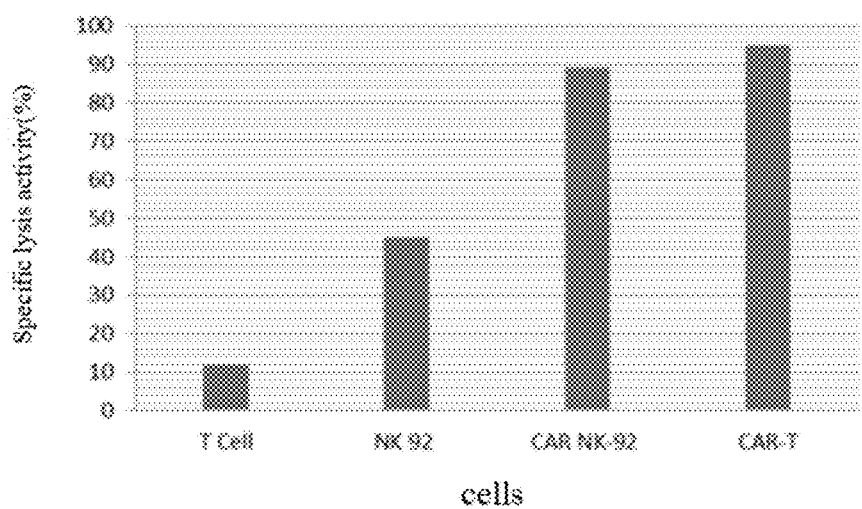
FIG. 4 illustrates an analysis result of the specific lysis activity of CAR-cells provided in Example 5 of the present invention.

The analysis result of the Specific lysis activity of the CAR cells is shown in FIG. 4, and the result shows that the constructed CAR-T cells and the CAR-NK-92 cells can remarkably kill tumor cells. The specific lysis activity was 95% and 83% respectively as shown in FIG. 4.

Example 6: In-Vivo Efficacy Testing of CAR Cells in Animal

1. Cell strain: H1299 lung cancer cell strain (hereinafter referred to as H1299 for short), stored in liquid nitrogen.

2. Experimental Animal 2. 1 Animal Species, Grade, Week Age, Weight and Source

NOG mouse, SPF grade, 4-6 weeks old when purchased, 15-25 g of body weight, purchased from Beijing Weitong Lihua Experimental Animal Co. ltd.

2. 2 Quarantine and domestication: quarantine inspection was performed by veterinarian after all animals being purchased. The animals were performed quarantine and domesticated for 2-7 days. Only those animals that were qualified by veterinary quarantine can be qualified for further experiment.

2. 3 Animal house: barrier animal house (SPF-grade), Suzhou GenePharma Co., Ltd.

2. 4 Animal feed, mouse feed (Standard SPF-grade). A nutrient component detection report of the feed was provided by production unit. After being purchased, the feed was subjected to ultraviolet irradiation disinfection and external packaging, and was followed by being placed into barrier environment for cryopreservation. The feed was taken one small packet (2.5 kg) each time, and weighed on demand amount, and then clamped and replaced. The feed should be used up within 2 weeks.

2. 5 Animal drinking water: SPF purified water, supplied by drinking water bottle. The animals have free access to water.

2. 6 Padding materials of animals: common poplar wood shavings, and use after high-pressure sterilization.

2. 7 Feeding Condition

The Animals were fed in polycarbonate cage box filled with padding material in individual room. Unless otherwise stated, the animals have free access to food the rest of time, and have free access to water.

In animal house, the room temperature ranged from 20-26° C. and humidity ranged from 40% to 70%, and experienced 12 hours of light at alternating light and darkness. The padding materials were replaced twice a week, and meanwhile, the feeding boxes were replaced. When there is serious contamination such as drinking water, urine, loose stools, etc, the feeding boxes would be replaced in time. The high-pressure disinfected drinking water bottles and bottle plugs were replaced every day. After being cleaned, all the replaced cages were sterilized by autoclaving.

The animal house floor was disinfected at least once every day, and the cage frames and animal house wall were disinfected at least once a week with 0.1% of bromogeramine or 0.5% of 84 disinfection solution, and the two disinfectant solutions were used interchangeably and generally alternated once every week.

3. Experimental Method 3. 1 Tumor Cell Culture and Concentration Configuration

Tumor cell culture: H1299 cells were cultured in DMEM culture solution containing 10% fetal calf serum. H1299 cells in the exponential growth phase were collected, and suspended in PBS and matrix glue (0.1 mL/animal) (the ratio of PBS to matrix glue is 1:1) for subcutaneous inoculation at a concentration of $5\times10^6$ cells/animal.

3. 2 Animal Grouping and Administration Dosage

The condition and the treatment of each group of animals were shown in the following table:

TABLE 1

Animal grouping and administration

| Group | Number of animals | Drug | administration mode |
|---|---|---|---|
| A | 8 | PBS | I.V. |
| B | 8 | T cell | I.V. |
| C | 8 | PD-1 protein extracellular domain or mutant thereof | I.V. |
| D | 8 | ROBO1 CAR-T(Preparation method can see patent application CN105907719A and PCT/CN2016/092578) | I.V. |
| E | 8 | ROBO1-(protein extracellular domain or mutant thereof) CAR-T (prepared by Example 3 of the present invention) | I.V. |

4. Detection Indicator 4. 1 General Clinical Observation

The observation time: one time every morning and every afternoon in one day.

Observation contents: tumor growth status and systemic status of rats were observed every two days after inoculation, and the contents included recording the formation time and growth status of tumor, and observed general activities, death, manure and the like of rats.

4. 2 Body Weight

Weighing time: the animal was weighed once at the time of being received, and weighed once a week after the start of the experiment, and weighed and recorded when the animals were dead or endangered.

Testing Animals: all animals 4. 3 Tumor Measurement

Figure 5:
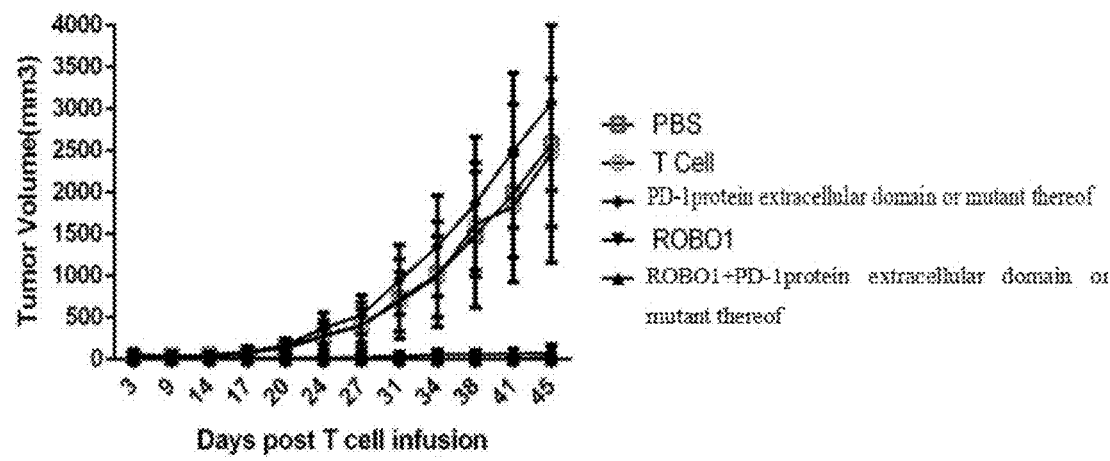
FIG. 5 illustrates a result of efficacy evaluation of the drug provided in Example 6 of the present invention in mouse tumor models.
Figure 6:
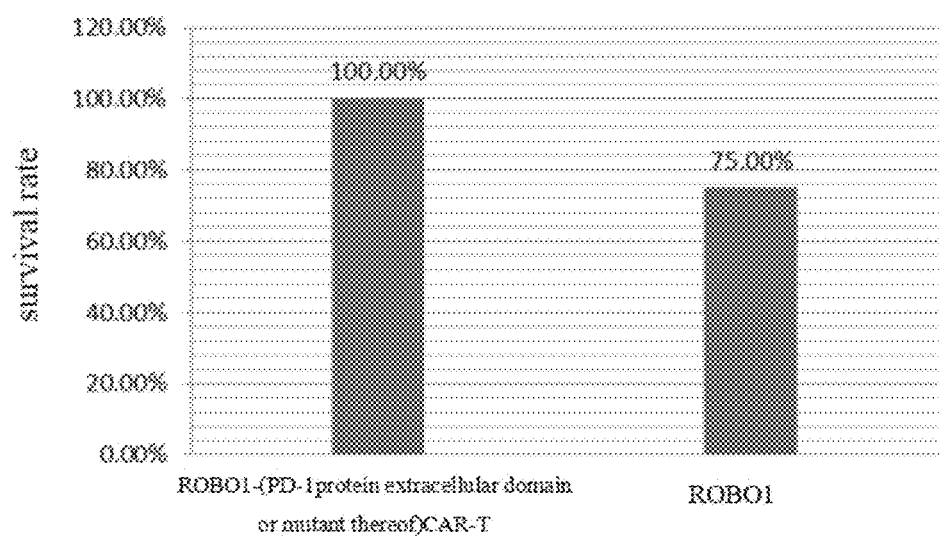
FIG. 6 illustrates the survival rate for ROBO1-(PD-1 protein extracellular domain or mutants thereof) CAR-T group and the ROBO1 CAR-T group, respectively, at the end point of the experiment provided in Example 6 of the present invention.
Figure 7:
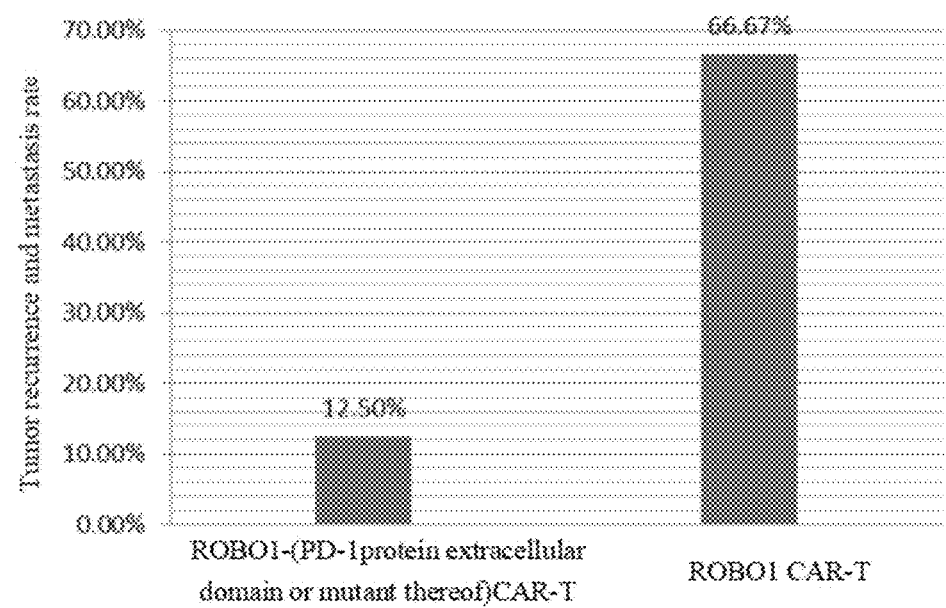
FIG. 7 illustrates the tumor recurrence rate for ROBO1-(PD-1 protein extracellular domain or mutants thereof) CAR-T group and the ROBO1 CAR-T group, respectively, at the end point of the experimental provided in Example 6 of the present invention.

The length diameter and short diameter of the tumor were measured by vernier caliper every two days, and the volume of the tumor was calculated as follows: the volume $(mm^3)=$ length diameter (mm)×short diameter $(mm^2)/2$. It's growth curve was depicted from the average value, as shown in FIG. 5.

5. Data Acquisition and Statistical Analysis 5. 1 Data Acquisition

The measured and observed result and data required for the scheme were recorded on appropriate tables by hand or the data can be acquired directly by computer.

5. 2 Data Analysis

Statistical software SPSS 20.0 was used to process data in the experiment, and the data were expressed by means of an average value±standard deviation. The specific analysis process was as follows:

The homogeneity of variance was checked by levene's test, and if the variance was homogeneous (P>0.05), statistical analysis was carried out in one-way ANOVA. If the ANOVA was statistically significant (P≤0.05), comparative analysis was carried out by LSD test (parameter method).

If the variance was not homogeneous (P≤0.05), kruskal-Walis test was used. If the kruskal-Wallis test has statistical significance (P≤0.05), comparison between any two means was carried out by Mann-Whitney method.

The result showed that the ROBO1-(PD-1 protein extracellular domain or mutant thereof) CAR-T group and ROBO1CAR-T group had significant killing tumor activity compared to the control group. However, when the animal tumor recurrence rate and animal survival rate of ROBO1-(PD-1 protein extracellular domain or mutant thereof) CAR-T group and ROBO1CAR-T group were compared at the end point of the experiment, the results showed that the recurrence rate for ROBO1-(PD-1 protein extracellular domain or mutant thereof)CAR-T group was 12.5% (recurrence occurred only in 1 mouse among 8 mice), and the survival rate was 100%. While the survival rate of the ROBO1CAR-T group was 75% (6 mice survived in 8 mice), the recurrence rate was 66.7% (Tumor recurrence occurred in 4 mice of the 6 survival mice). The result showed that the introduction of PD-1 protein extracellular domain or mutant molecules of blocking the PD-1 and PD-La into CAR structure, can significantly reduce the tumor recurrence after the tumor was treated with CAR, and meanwhile has remarkable significance on improvement of the safety of CAR drugs.

The above descriptions are only preferred embodiments of the present invention, and are not intended to limit the present invention. Any modification, equivalent replacement and the like falling within the spirit and principle of the present invention, should be all included within the protection scope of the invention.

What is claimed is:

1. A polynucleotide comprising a nucleotide encoding chimeric antigen receptor and a nucleotide encoding extracellular secretory protein, wherein the chimeric antigen receptor comprises an antigen-binding domain, a transmembrane domain and a costimulatory signaling region, and the antigen-binding domain is capable of specifically binding to FN3 domain of the tumor specific antigen ROBO1, and activating immune cells through the transmembrane domain and the costimulatory signaling region; the extracellular secretory protein is capable of preventing or inhibiting the binding of the wild type PD-1 protein to PD-L1 ligand;

wherein, the extracellular secretory protein is the extracellular domain of PD-1 protein or the mutant of the extracellular domain, and the mutant of the extracellular domain is capable of binding PD-L1 with high affinity;

wherein, the polynucleotide is a nucleotide encoding anti-ROBO1-FN3 scFv-CD8 transmembrane-4-1BB-CD3ζ-IRES-(the extracellular domain of PD-1 protein or mutant thereof), which has a sequence as shown in SEQ ID NO: 7.

2. The polynucleotide according to claim 1, wherein the antigen-binding domain is an antigen-binding fragment, and the antigen-binding fragment is scFv; the anti-ROBO1-FN3 scFv has an amino acid sequence as shown in SEQ ID NO:9; and/or, the extracellular domain or the mutant thereof has an amino acid sequence as shown in SEQ ID NO: 8.

3. The polynucleotide according to claim 2, wherein the nucleotide encoding antigen-binding domain has a sequence as shown in SEQ ID NO: 2; and/or, the nucleotide encoding the extracellular domain or the mutant thereof has a sequence as shown in SEQ ID NO: 1.

4. The polynucleotide according to claim 1, wherein the nucleotide encoding chimeric antigen receptor and the nucleotide encoding extracellular secretory protein are not in the same reading frame; and/or, wherein the nucleotide encoding IRES (internal ribosome entry site) is located between the nucleotide encoding chimeric antigen receptor and the nucleotide encoding extracellular secretory protein, and the IRES-encoding nucleotide has a sequence as shown in SEQ ID NO: 3.

5. The polynucleotide according to claim 1, wherein the CD8 transmembrane domain has a sequence as shown in SEQ ID NO:10; and/or, the 4-1BB intracellular domain has a sequence as shown in SEQ ID NO: 11; the CD3ζ intracellular domain has a sequence as shown in SEQ ID NO:12.

6. The polynucleotide according to claim 5, wherein the nucleotide encoding the CD8 transmembrane domain has a sequence as shown in SEQ ID NO: 4; and/or, the nucleotide encoding 4-1BB intracellular domain has a sequence as shown in SEQ ID NO: 5, and/or, the coding nucleotide of CD3ζ intracellular domain has a sequence as shown in SEQ ID NO: 6.

7. The polynucleotide according to claim 1, wherein the polynucleotide comprises a nucleotide encoding anti-ROBO1-FN3 scFv-CD8 transmembrane-4-1BB-CD3ζ, which has a sequence as shown in SEQ ID NO: 13.

8. A pharmaceutical composition comprising one or more of the polynucleotide according to claim 1.

* * * * *

```
                        SEQUENCE LISTING

<160> NUMBER OF SEQ ID NOS: 13

<210> SEQ ID NO 1
<211> LENGTH: 525
<212> TYPE: DNA
<213> ORGANISM: Unknown
<220> FEATURE:
<223> OTHER INFORMATION: nucleotide encoding extracellular domain or the
      mutant of PD-1 protein

<400> SEQUENCE: 1
atggagaccg acaccctgct cctgtgggtg ctgctgctgt gggtgcctgg cagcacagga      60
ggaggcggag gttctcctgg ctggttcctg gacagcccg ataggccctg gaatcccccc     120
acctttagcc ctgccctgct ggtggtgaca gagggcgaca acgccacctt cacctgctcc    180
ttcagcaaca cctccgagag ctttcacgtg gtgtggcaca gggagtcccc tagcggacag    240
accgataccc tggccgcctt ccctgaggac agaagccagc ccggccagga ctgtaggttc    300
agagtgacac agctgcccaa cggcagggac ttccacatga gcgtggtgag ggccaggagg    360
aacgactccg gcacctacgt gtgcggcgtg atcagcctgg ccccaagat ccagatcaag     420 gagagcctga gagccgagct gagggtgacc gagaggagag ccgaagtgcc caccgcccat    480
cctagcccta gccccagacc tgccggccag ttccagaccc tggtg                    525

<210> SEQ ID NO 2
<211> LENGTH: 708
<212> TYPE: DNA
<213> ORGANISM: Unknown
<220> FEATURE:
<223> OTHER INFORMATION: nucleotide encoding antigen-binding domain

<400> SEQUENCE: 2
atccagatga cacagactac atcctccctg tctgcctctc tgggagacag agtcaccatc     60
agttgcaggg caagtcagga cattagcaat tttttaaact ggtatcagca gaaaccagat    120
ggaactgtta aactcctgat ctactacaca tcaagattac attctggagt cccatcaagg    180
ttcagtggca gtgggtctgg aacagatttt tctctcacca ttagcaaact ggagcaagaa    240
gatattgcca cttacttttg ccaacagggt aatacgcttc cacttacgtt cggcgctggg    300
acaaagttgg aacttaaagg tggtggtggt tctggcggcg gcggctccgg aggaggagga    360
tcgctgcaac agtctggacc tgagttggtg aagcctgggg cttcagtgaa gatttcctgc    420
aaggcttctg gatacacatt cactgactac tacatgaatt gggtgaagct tagccatgga    480
```

```
aagagccttg agtggattgg agatattgtt cctaacaatg gtgatactac ttacaaccag        540
aatttcagag gcaaggccac attgactgta gacaagtcct ccagcacagc ctacatggag        600
ctccgcagcc tgacatctga ggactctgca gtctattact gtgcaagatt cagtaattac        660
gtttacccct ttgactactg gggccaaggc accactatca cagtctcc                    708

<210> SEQ ID NO 3
<211> LENGTH: 521
<212> TYPE: DNA
<213> ORGANISM: Unknown
<220> FEATURE:
<223> OTHER INFORMATION: IRES nucleotide

<400> SEQUENCE: 3
ggccggtgtg cgtttgtcta tatgttattt tccaccatat tgccgtcttt tggcaatgtg         60
agggcccgga aacctggccc tgtcttcttg acgagcattc ctaggggtct ttcccctctc        120
gccaaaggaa tgcaaggtct gttgaatgtc gtgaaggaag cagttcctct ggaagcttct        180
tgaagacaaa caacgtctgt agcgaccctt gcaggcagc  ggaaccccccc acctggcgac        240 aggtgcctct gcggccaaaa gccacgtgta taagatacac ctgcaaaggc ggcacaaccc        300
cagtgccacg ttgtgagttg gatagttgtg gaaagagtca atggctcac ctcaagcgta        360 ttcaacaagg gctgaagga tgcccagaag gtaccccatt gtatgggatc tgatctgggg        420
cctcggtgca catgctttac atgtgtttag tcgaggttaa aaaacgtcta ggccccccga        480
accacgggga cgtggttttc ctttgaaaaa cacgatgata a                            521

<210> SEQ ID NO 4
<211> LENGTH: 72
<212> TYPE: DNA
<213> ORGANISM: Unknown
<220> FEATURE:
<223> OTHER INFORMATION: nucleotide encoding CD8TM domain

<400> SEQUENCE: 4
atctacatct gggcgccctt ggccgggact tgtggggtcc ttctcctgtc actggttatc         60 acccttact gc                                                             72

<210> SEQ ID NO 5
<211> LENGTH: 126
<212> TYPE: DNA
<213> ORGANISM: Unknown
<220> FEATURE:
<223> OTHER INFORMATION: nucleotide encoding 4-1BB intracellular domain

<400> SEQUENCE: 5
aaacggggca gaaagaaact cctgtatata ttcaaacaac catttatgag accagtacaa         60
actactcaag aggaagatgg ctgtagctgc cgatttccag aagaagaaga aggaggatgt        120
gaactg                                                                   126

<210> SEQ ID NO 6
<211> LENGTH: 336
<212> TYPE: DNA
<213> ORGANISM: Unknown
<220> FEATURE:
<223> OTHER INFORMATION: nucleotide encoding CD3??intracellular domain

<400> SEQUENCE: 6
agagtgaagt tcagcaggag cgcagacgcc cccgcgtacc agcagggcca gaaccagctc         60
```

| | |
|---|---|
| tataacgagc tcaatctagg acgaagagag gagtacgatg ttttggacaa gagacgtggc | 120 |
| cgggaccctg agatggggg aaagccgaga aggaagaacc ctcaggaagg cctgtacaat | 180 |
| gaactgcaga aagataagat ggcggaggcc tacagtgaga ttgggatgaa aggcgagcgc | 240 |
| cggaggggca aggggcacga tggcctttac cagggtctca gtacagccac caaggacacc | 300 |
| tacgacgccc ttcacatgca ggccctgccc cctcgc | 336 |

<210> SEQ ID NO 7
<211> LENGTH: 2545
<212> TYPE: DNA
<213> ORGANISM: Unknown
<220> FEATURE:
<223> OTHER INFORMATION: nucleotide encoding anti-ROBO1-FN3
scFv-CD8TM-4-1BB-CD3??-IRES-(PD-1protein extracellular domain or
mutant thereof)

<400> SEQUENCE: 7

| | |
|---|---|
| atggccctgc ctgtgacagc cctgctgctg cctctggctc tgctgctgca tgccgctaga | 60 |
| cccatccaga tgacacagac tacatcctcc ctgtctgcct ctctgggaga cagagtcacc | 120 |
| atcagttgca gggcaagtca ggacattagc aattttttaa actggtatca gcagaaacca | 180 |
| gatggaactg ttaaactcct gatctactac acatcaagat acattctgg agtcccatca | 240 |
| aggttcagtg gcagtgggtc tggaacagat ttttctctca ccattagcaa actggagcaa | 300 |
| gaagatattg ccacttactt ttgccaacag gtaatacgc ttccacttac gttcggcgct | 360 |
| gggacaaagt tggaacttaa aggtggtggt ggttctggcg gcggcggctc cggaggagga | 420 |
| ggatcgctgc aacagtctgg acctgagttg gtgaagcctg ggcttcagt gaagatttcc | 480 |
| tgcaaggctt ctggatacac attcactgac tactacatga attgggtgaa gcttagccat | 540 |
| ggaaagagcc ttgagtggat tggagatatt gttcctaaca atggtgatac tacttacaac | 600 |
| cagaatttca gaggcaaggc cacattgact gtagacaagt cctccagcac agcctacatg | 660 |
| gagctccgca gcctgacatc tgaggactct gcagtctatt actgtgcaag attcagtaat | 720 |
| tacgtttacc cttttgacta ctggggccaa ggcaccacta tcacagtctc caccacgacg | 780 |
| ccagcgccgc gaccaccaac accggcgccc accatcgcgt cgcagcccct gtccctgcgc | 840 |
| ccagaggcgt gccggccagc ggcgggggc gcagtgcaca cgagggggct ggacttcgcc | 900 |
| tgtgatatct acatctgggc gcccttggcc gggacttgtg gggtccttct cctgtcactg | 960 |
| gttatcaccc tttactgcaa acggggcaga aagaaactcc tgtatatatt caaacaacca | 1020 |
| tttatgagac cagtacaaac tactcaagag gaagatggct gtagctgccg atttccagaa | 1080 |
| gaagaagaag aggatgtgaa ctgagagtg aagttcagca ggagcgcaga cgcccccgcg | 1140 |
| taccagcagg gccagaacca gctctataac gagctcaatc taggacgaag agaggagtac | 1200 |
| gatgtttggg acaagagacg tggccgggac cctgagatgg ggggaaagcc gagaaggaag | 1260 |
| aaccctcagg aaggcctgta caatgaactg cagaaagata gatggcgga ggcctacagt | 1320 |
| gagattggga tgaaaggcga gcgccggagg ggcaaggggc acgatggcct ttaccagggt | 1380 |
| ctcagtacag ccaccaagga cacctacgac gccttcaca tgcaggccct gcccctcgc | 1440 |
| taagcccctc tccctccccc ccccctaacg ttactggccg aagccgcttg gaataaggcc | 1500 |
| ggtgtgcgtt tgtctatatg ttattttcca ccatattgcc gtcttttggc aatgtgaggg | 1560 |
| cccggaaacc tggccctgtc ttcttgacga gcattcctag gggtctttcc cctctcgcca | 1620 |
| aaggaatgca aggtctgttg aatgtcgtga aggaagcagt tcctctggaa gcttcttgaa | 1680 |
| gacaaacaac gtctgtagcg accctttgca ggcagcggaa ccccccacct ggcgacaggt | 1740 |

```
gcctctgcgg ccaaaagcca cgtgtataag atacacctgc aaaggcggca acccccagt    1800 gccacgttgt gagttggata gttgtggaaa gagtcaaatg gctcacctca agcgtattca    1860
acaaggggct gaaggatgcc cagaaggtac cccattgtat gggatctgat ctggggcctc    1920
ggtgcacatg ctttacatgt gtttagtcga ggttaaaaaa cgtctaggcc ccccgaacca    1980
cggggacgtg gttttccttt gaaaaacacg atgataaatg gagaccgaca ccctgctcct    2040
gtgggtgctg ctgctgtggg tgcctggcag cacaggagga ggcggaggtt ctcctggctg    2100
gttcctggac agccccgata ggccctggaa tccccccacc tttagccctg ccctgctggt    2160
ggtgacagag ggcgacaacg ccaccttcac ctgctccttc agcaacacct ccgagagctt    2220
tcacgtggtg tggcacaggg agtcccctag cggacagacc gatacccctgg ccgccttccc    2280 tgaggacaga agccagcccg gccaggactg taggttcaga gtgacacagc tgcccaacgg    2340
cagggacttc cacatgagcg tggtgagggc caggaggaac gactccggca cctacgtgtg    2400
cggcgtgatc agcctggccc ccaagatcca gatcaaggag agcctgagag ccgagctgag    2460
ggtgaccgag aggagagccg aagtgcccac cgcccatcct agccctagcc ccagacctgc    2520
cggccagttc agaccctggg tgtaa                                          2545
```

<210> SEQ ID NO 8
<211> LENGTH: 175
<212> TYPE: PRT
<213> ORGANISM: Unknown
<220> FEATURE:
<223> OTHER INFORMATION: extracellular domain of PD-1 protein

<400> SEQUENCE: 8

Met Glu Thr Asp Thr Leu Leu Leu Trp Val Leu Leu Leu Trp Val Pro
1               5                   10                  15

Gly Ser Thr Gly Gly Gly Gly Ser Pro Gly Trp Phe Leu Asp Ser
            20                  25                  30

Pro Asp Arg Pro Trp Asn Pro Pro Thr Phe Ser Pro Ala Leu Leu Val
        35                  40                  45

Val Thr Glu Gly Asp Asn Ala Thr Phe Thr Cys Ser Phe Ser Asn Thr
    50                  55                  60

Ser Glu Ser Phe His Val Val Trp His Arg Glu Ser Pro Ser Gly Gln
65                  70                  75                  80

Thr Asp Thr Leu Ala Ala Phe Pro Glu Asp Arg Ser Gln Pro Gly Gln
                85                  90                  95

Asp Cys Arg Phe Arg Val Thr Gln Leu Pro Asn Gly Arg Asp Phe His
            100                 105                 110

Met Ser Val Val Arg Ala Arg Arg Asn Asp Ser Gly Thr Tyr Val Cys
        115                 120                 125

Gly Val Ile Ser Leu Ala Pro Lys Ile Gln Ile Lys Glu Ser Leu Arg
    130                 135                 140

Ala Glu Leu Arg Val Thr Glu Arg Arg Ala Glu Val Pro Thr Ala His
145                 150                 155                 160

Pro Ser Pro Ser Pro Arg Pro Ala Gly Gln Phe Gln Thr Leu Val
                165                 170                 175

<210> SEQ ID NO 9
<211> LENGTH: 236
<212> TYPE: PRT
<213> ORGANISM: Unknown
<220> FEATURE:
<223> OTHER INFORMATION: amino acid sequence of anti-ROBO1-FN3scFv

<400> SEQUENCE: 9

Ile Gln Met Thr Gln Thr Thr Ser Ser Leu Ser Ala Ser Leu Gly Asp
1               5                   10                  15

Arg Val Thr Ile Ser Cys Arg Ala Ser Gln Asp Ile Ser Asn Phe Leu
            20                  25                  30

Asn Trp Tyr Gln Gln Lys Pro Asp Gly Thr Val Lys Leu Leu Ile Tyr
        35                  40                  45

Tyr Thr Ser Arg Leu His Ser Gly Val Pro Ser Arg Phe Ser Gly Ser
    50                  55                  60

Gly Ser Gly Thr Asp Phe Ser Leu Thr Ile Ser Lys Leu Glu Gln Glu
65                  70                  75                  80

Asp Ile Ala Thr Tyr Phe Cys Gln Gln Gly Asn Thr Leu Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Ser Leu Gln Gln Ser Gly Pro Glu
        115                 120                 125

Leu Val Lys Pro Gly Ala Ser Val Lys Ile Ser Cys Lys Ala Ser Gly
130                 135                 140

Tyr Thr Phe Thr Asp Tyr Tyr Met Asn Trp Val Lys Leu Ser His Gly
145                 150                 155                 160

Lys Ser Leu Glu Trp Ile Gly Asp Ile Val Pro Asn Asn Gly Asp Thr
                165                 170                 175

Thr Tyr Asn Gln Asn Phe Arg Gly Lys Ala Thr Leu Thr Val Asp Lys
            180                 185                 190

Ser Ser Ser Thr Ala Tyr Met Glu Leu Arg Ser Leu Thr Ser Glu Asp
        195                 200                 205

Ser Ala Val Tyr Tyr Cys Ala Arg Phe Ser Asn Tyr Val Tyr Pro Phe
210                 215                 220

Asp Tyr Trp Gly Gln Gly Thr Thr Ile Thr Val Ser
225                 230                 235

<210> SEQ ID NO 10
<211> LENGTH: 24
<212> TYPE: PRT
<213> ORGANISM: Unknown
<220> FEATURE:
<223> OTHER INFORMATION: CD8TM domain

<400> SEQUENCE: 10

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 11
<211> LENGTH: 42
<212> TYPE: PRT
<213> ORGANISM: Unknown
<220> FEATURE:
<223> OTHER INFORMATION: 4-1BB intracellular domain

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 12
<211> LENGTH: 112
<212> TYPE: PRT
<213> ORGANISM: Unknown
<220> FEATURE:
<223> OTHER INFORMATION: CD3?? intracellular domain

<400> SEQUENCE: 12

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 13
<211> LENGTH: 1440
<212> TYPE: DNA
<213> ORGANISM: Unknown
<220> FEATURE:
<223> OTHER INFORMATION: sequence of anti-ROBO1-FN3 scFv-CD8TM-4-1BB-
      CD3??

<400> SEQUENCE: 13
atggccctgc ctgtgacagc cctgctgctg cctctggctc tgctgctgca tgccgctaga      60
cccatccaga tgacacagac tacatcctcc ctgtctgcct ctctgggaga cagagtcacc     120
atcagttgca gggcaagtca ggacattagc aatttttta actggtatca gcagaaacca     180
gatggaactg ttaaactcct gatctactac acatcaagat acattctgg agtcccatca     240 aggttcagtg gcagtgggtc tggaacagat ttttctctca ccattagcaa actggagcaa     300
gaagatattg ccacttactt tgccaacag ggtaatacgc ttccacttac gttcggcgct     360
gggacaaagt tggaacttaa aggtggtggt ggttctggcg gcggcggctc cggaggagga     420
ggatcgctgc aacagtctgg acctgagttg gtgaagcctg gggcttcagt gaagatttcc     480
tgcaaggctt ctggatacac attcactgac tactacatga attgggtgaa gcttagccat     540
ggaaagagcc ttgagtggat tggagatatt gttcctaaca atggtgatac tacttacaac     600
cagaatttca gaggcaaggc cacattgact gtagacaagt cctccagcac agcctacatg     660
gagctccgca gcctgacatc tgaggactct gcagtctatt actgtgcaag attcagtaat     720
tacgtttacc cttttgacta ctgggccaa ggcaccacta tcacagtctc caccacgacg     780
ccagcgccgc gaccaccaac accggcgccc accatcgcgt cgcagcccct gtcctgcgc     840 ccagaggcgt gccggccagc ggcgggggc gcagtgcaca cgagggggct ggacttcgcc     900
tgtgatatct acatctgggc gcccttggcc gggacttgtg ggtccttct cctgtcactg     960 gttatcaccc tttactgcaa acggggcaga aagaaactcc tgtatatatt caaacaacca    1020

```
tttatgagac cagtacaaac tactcaagag gaagatggct gtagctgccg atttccagaa    1080
gaagaagaag gaggatgtga actgagagtg aagttcagca ggagcgcaga cgcccccgcg    1140
taccagcagg gccagaacca gctctataac gagctcaatc taggacgaag agaggagtac    1200
gatgttttgg acaagagacg tggccgggac cctgagatgg ggggaaagcc gagaaggaag    1260
aaccctcagg aaggcctgta caatgaactg cagaaagata agatggcgga ggcctacagt    1320
gagattggga tgaaaggcga gcgccggagg ggcaaggggc acgatggcct ttaccagggt    1380
ctcagtacag ccaccaagga cacctacgac gcccttcaca tgcaggccct gccccctcgc    1440
```